(12) United States Patent
Uematsu et al.

(10) Patent No.: US 6,530,874 B2
(45) Date of Patent: Mar. 11, 2003

(54) SYNCHRONIZED MOVING SHIELD FOR A RADIATION THERAPY APPARATUS

(75) Inventors: Minoru Uematsu, 651 Yamanouchi, Kamakura-shi, Kanagawa-ken (JP); Hiroshi Ueda, Tokyo (JP)

(73) Assignees: Minoru Uematsu, Kanagawa-ken (JP); Euro Meditech Co., Ltd., Tokyo (JP); Hitk Enterprise Corp., Tokyo (JP)

( * ) Notice: Subject to any disclaimer, the term of this patent is extended or adjusted under 35 U.S.C. 154(b) by 72 days.

(21) Appl. No.: 09/739,099

(22) Filed: Dec. 19, 2000

(65) Prior Publication Data

US 2001/0027260 A1 Oct. 4, 2001

(30) Foreign Application Priority Data

Mar. 29, 2000 (JP) .......................................... 2000-091059

(51) Int. Cl.$^7$ ................................................. A61N 5/01
(52) U.S. Cl. ............................. 600/1; 378/65; 378/145; 378/146; 378/147; 378/203; 378/205
(58) Field of Search ................................ 600/1; 378/65, 378/145, 146, 147, 203, 205

(56) References Cited

U.S. PATENT DOCUMENTS

| 4,096,391 A | * | 6/1978 | Barnes ........................ 378/146 |
| 4,118,631 A | | 10/1978 | Froggatt ...................... 250/492 |
| 5,396,533 A | | 3/1995 | Holzermer .................... 578/150 |
| 5,745,545 A | | 4/1998 | Hughes ......................... 378/65 |
| 6,055,295 A | * | 4/2000 | Murthy et al. .............. 378/145 |

* cited by examiner

Primary Examiner—Charles G. Freay
Assistant Examiner—Emmanuel Sayoc
(74) Attorney, Agent, or Firm—Birch, Stewart, Kolasch & Birch, LLP

(57) ABSTRACT

A synchronized moving radiation shield apparatus includes at least one shielding block disposed under a radiation pathway of a radiation therapy unit in such a manner that a radiation field is formed with the shielding block, wherein an affected portion of a person is exposed to radiation through the radiation field while radiation therapy of a portion, other than the affected portion, of the person, is shielded by the shielding block. The apparatus further includes a movable portion for movably holding the shielding block while not blocking the passing of radiation through the radiation field; drive means, connected to the movable portion, for moving the radiation field to a specific position; and control means for controlling the drive means in such a manner that the radiation field is movable in matching to a variation in position of the affected portion. With this configuration, since the radiation field is moved in accordance with the motion of the affected portion during radiation therapy for carcinoma, it is possible to prevent radiation therapy of adjacent normal portions, and hence to improve the treatment results by increasing the radiation doses for the affected portion.

5 Claims, 5 Drawing Sheets

SYNCHRONIZED MOVING SHIELD FOR A RADIATION THERAPY APPARATUS

BACKGROUND OF THE INVENTION

The present invention relates to a synchronized moving radiation shield apparatus including at least one shield block disposed under a radiation pathway of a radiation therapy unit used for radiation therapy for carcinomas in such a manner that a radiation field is formed with the shielding block, wherein an affected portion of a person is exposed to radiation through the radiation field while radiation therapy of a portion, other than the affected portion, of the person, is shielded by the shielding block. In particular, the present invention relates to a synchronized moving radiation shield apparatus configured such that radiation therapy of a portion, other than an affected portion, of a person is shielded by moving the radiation field in matching to the motion of the affected portion when the affected portion is subjected to radiation therapy.

A known radiation therapy unit used for radiation therapy for carcinomas or benign lesions is configured to have a lead block as a radiation shielding substance which is fixedly mounted to the unit in such a manner that a radiation field corresponding to an affected portion or a target is formed in the lead block, wherein the affected portion is subjected to radiation therapy through the radiation field and radiation therapy of a portion other than the affected portion is shielded by the lead block.

The above radiation therapy unit, however, has a problem. For example, for a patient having an affected portion in the lung, since the position of the affected portion is shifted by respiratory motion, adjacent normal portions of the affected portion should be exposed to radiation during radiation therapy of the affected portion. Accordingly, in consideration of radiation injury to adjacent normal portions of the patient, total radiation doses or daily fraction sizes must be limited, so that the affected portion may not be irradiated with sufficient doses.

SUMMARY OF THE INVENTION

An object of the present invention is to provide a synchronized moving radiation shield apparatus for shielding radiation therapy of a portion other than a moving affected portion of a patient to be exposed to radiation by moving a radiation field in accordance with the motion of the affected portion due to respiratory motion.

To achieve the above object, according to the present invention, there is provided a synchronized moving radiation shield apparatus including at least one shielding block disposed under a radiation pathway of a radiation therapy unit in such a manner that a radiation field is formed with the shielding block, wherein an affected portion of a person is exposed to radiation through the radiation field while radiation therapy of a portion, other than the affected portion, of the person, is shielded by the shielding block, the radiation shielding apparatus including: a movable portion for movably holding the shielding block while not blocking the passing of radiation through the radiation field; drive means, connected to the movable portion, for moving the radiation field to a specific position; and control means for controlling the drive means in such a manner that the radiation field is moving in matching to a variation in position of the affected portion.

With this configuration, it is possible to move the radiation field formed with the shielding block held by the movable portion in matching to the motion of an affected portion in which a lesion such as carcinoma necessary for radiation therapy has grown, that is, a target, by supplying a command corresponding to the motion of the affected portion to the drive means by the control means, and hence to prevent radiation therapy of a portion other than the affected portion even if the affected portion is moved in the body of a patient by respiratory motion upon radiation therapy for the patient.

Here, there may be adopted a configuration in which the motion of the affected portion is previously sampled and the sampled data is patterned, and the shielding block is moved in such a manner that the radiation field is moved on the basis of the patterned motion of the affected portion; however, according to the present invention, preferably, the control means controls the drive means in such a manner that the radiation field is located at a position corresponding to the affected portion while sequentially estimating the motion of the affected portion.

With this configuration, since the shielding block can be moved in such a manner that the radiation field is moved while following the motion of the affected portion, it is possible to more accurately perform the radiation therapy to only the affected portion. Preferably, the synchronized moving radiation shield apparatus further includes detecting means for sequentially detecting a variation in position of part of a body of the person correlated to the motion of the affected portion; wherein the control means comprises a microprocessor for automatically controlling the drive means on the basis of a detection value of the detecting means in accordance with a program for realizing alignment of the affected portion to he radiation field.

With this configuration, the microprocessor can effectively, instantly decide the movement direction and stoppage of the drive means in matching to a variation in position of the affected portion by sequentially measuring a change in oscillation of part of the body such as a chest wall varied depending on respiratory motion at significantly short intervals, that is, substantially continuously during radiation therapy by using a high resolution instrument such as a high speed measuring laser displacement gauge.

The movable portion preferably includes a base plate having a hole at a position matched to a movable range of the radiation field and fixed under the radiation therapy unit; rails provided on the upper surface of the base plate; and a movable plate having a hole at a position corresponding to the radiation field and movably disposed on the rails; wherein the shielding block is mounted on the movable plate in such a manner that the radiation field is formed with the shielding block, and the movable plate is moved on the rails by the drive means.

With this configuration, since the movable plate is moved along the rails by the drive means, it is possible to easily set the movement position of the shielding block and enhance the positional accuracy. In this case, since the movable plate has the hole at the position corresponding to the radiation field and also the base plate has the hole at the position matched to the movable range of the radiation field, the passing of the radiation through the radiation field is not obstructed.

Here, according to the present invention, in the case where the movable portion is configured such that the movable plate is movable along the rails as described above, if one set of the drive means and the movable plate on the rails are prepared, the shielding block can be horizontally moved along the longitudinal direction or X-direction; and if two sets of the movable plates on the rails and the drive means are prepared in such a manner that the base plate of the first movable portion is fixed to the radiation therapy unit, the base plate of the second base portion is mounted on the movable plate of the first movable portion with the rails of the first and second movable portions disposed in perpendicular to each other, and the shielding block is mounted on the movable plate of the second movable portion, the shielding block can be horizontally moved in the longitudinal and lateral directions or XY-directions. In the case of moving the shielding block in the XY-directions, the movable plate of the first or lower movable portion may be integrated with the base plate of the second or upper movable portion. Similarly, the shielding block can be configured to be movable in the three-dimensional directions or XYZ-directions.

The drive means is preferably composed of a stepping motor revolving on the basis of a pulse signal fed from the control means.

With this configuration, since the stepping motor or pulse motor accurately revolves and stops on the basis of a pulse signal fed from the control means with occurrence of little runout, the radiation field can be accurately moved in matching to the motion of the affected portion. To be more specific, even if a signal corresponding to a variation in the affected portion is continuously inputted in the microprocessor at very short intervals and is instantly converted into a pulse signal outputted as a command to the stepping motor, the motor can be accurately moved on the basis of the command with little runout. As a result, it is possible to accurately move the movable portion substantially in accordance with the motion of the affected portion.

The synchronized moving radiation shield apparatus preferably further includes detecting means for detecting the fact that the movable means is moved up to a critical position of the movable range.

With this configuration, even if there occurs any trouble, it is possible to prevent over-run of the movable portion.

DETAILED DESCRIPTION OF THE PREFERRED EMBODIMENTS

Figure 1:
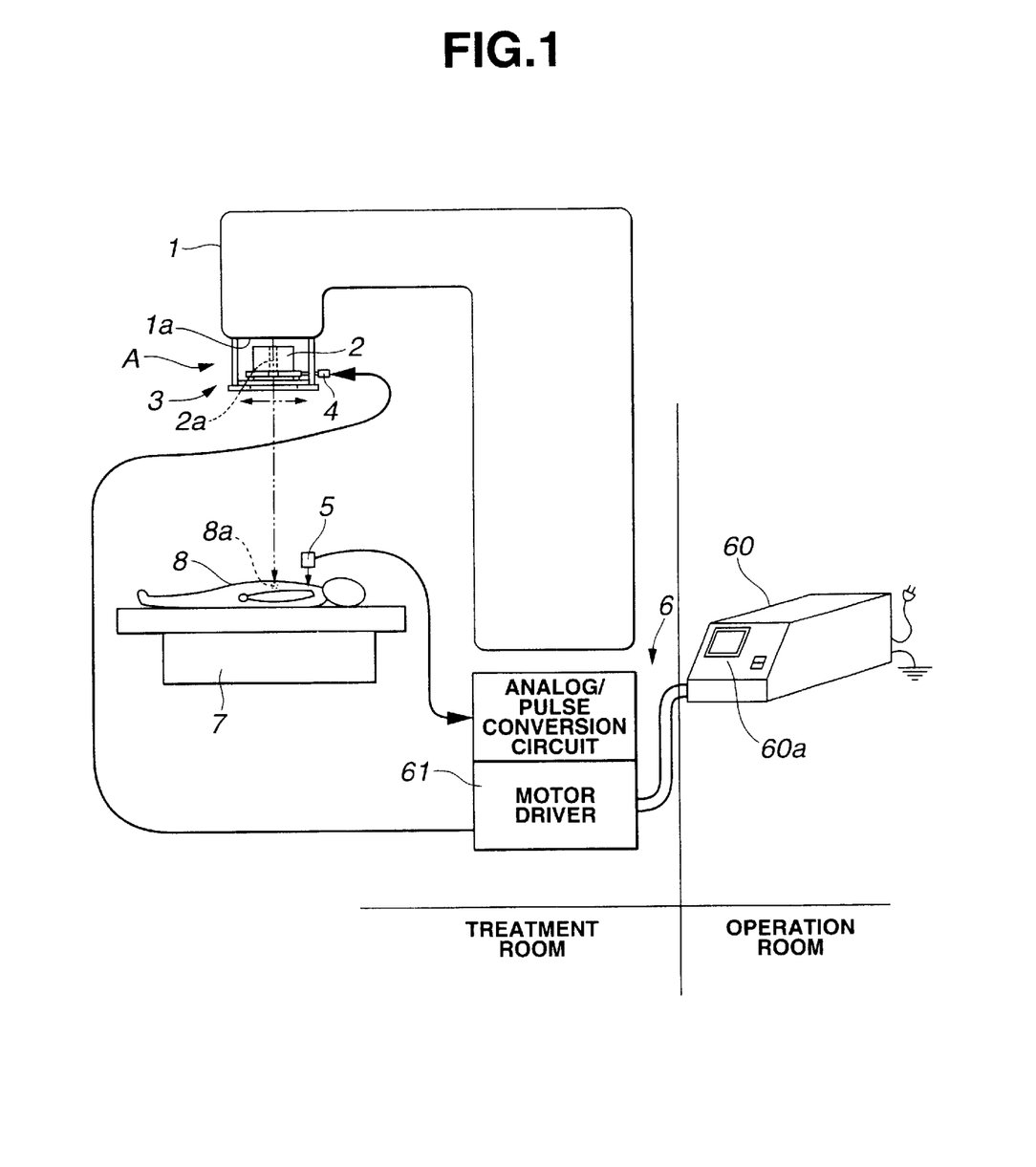
FIG. 1 is a schematic diagram illustrating an embodiment of a synchronized moving radiation shield apparatus of the present invention.
Figure 2:
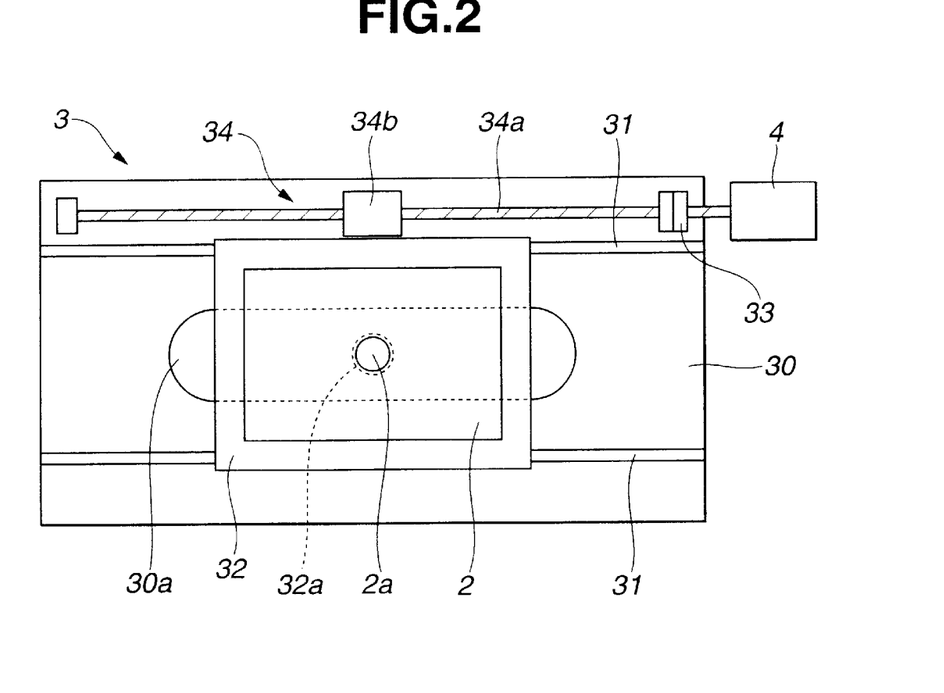
FIG. 2 is a plan view illustrating a configuration of a movable portion of the synchronized moving radiation shield apparatus shown in FIG. 1.
Figure 3:
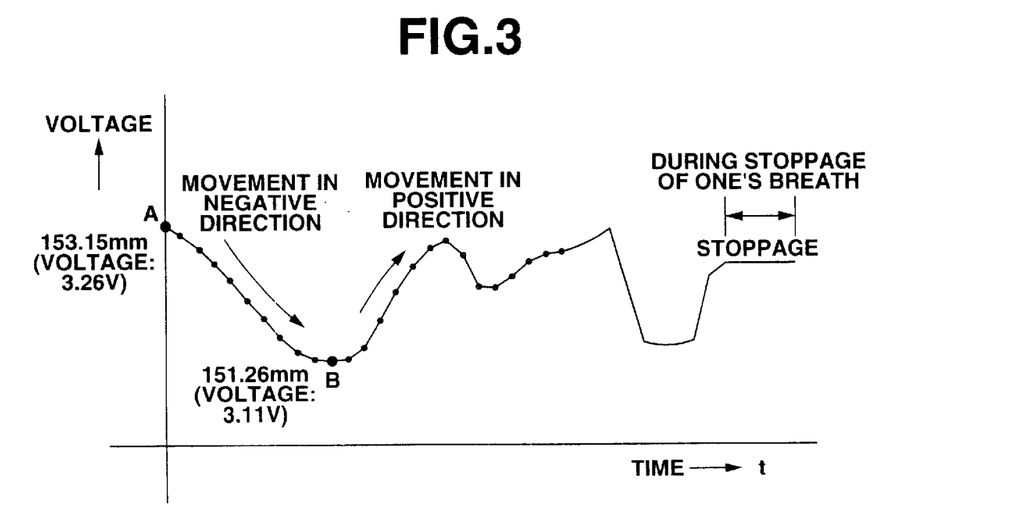
FIG. 3 is a graph illustrating control means of the synchronized moving radiation shield apparatus shown in FIG. 1.
Figure 4:
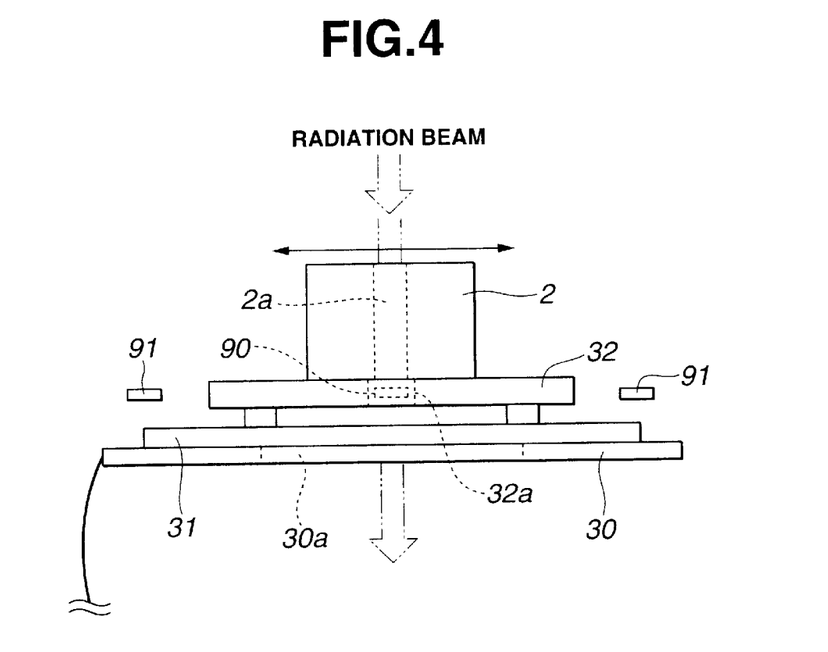
FIG. 4 is a schematic front view illustrating an application example of the synchronized moving radiation shield apparatus shown in FIG. 1.

Hereinafter, embodiments of the present invention will be described with reference to the drawings. FIGS. 1 to 4 are views illustrating an embodiment of a synchronized moving radiation shield apparatus A of the present invention, wherein FIG. 1 is a schematic view showing the entire configuration of the synchronized moving radiation shield apparatus mounted on a radiation therapy unit; FIG. 2 is an enlarged plan view of a movable portion of the synchronized moving radiation shield apparatus illustrating the configuration of the movable portion; FIG. 3 is a graph illustrating control means of the synchronized moving radiation shield apparatus; and FIG. 4 is a schematic front view illustrating an application example of the synchronized moving radiation shield apparatus.

The synchronized moving radiation shield apparatus A, which is mounted under a beam pathway 1a of a radiation therapy unit 1, includes a shielding block 2 with which a radiation field 2a is formed. A radiation beam is allowed to pass through the radiation field 2a of the shielding block 2 to subject only an affected portion to radiation therapy while shielding radiation therapy of a portion other than the affected portion by the shielding block 2.

The synchronized moving radiation shield apparatus A includes a movable portion 3 on which the shield block 2 is mounted, a stepping motor 4 interconnected to the movable portion 3, a laser displacement gauge 5, and control means 6 configured as a microprocessor contained in a relay control box 61. The control means 6 performs analog/pulse conversion of detection signals fed from a sequence controller for controlling the entire unit and the laser displacement gauge 5, and controls the stepping motor 4 and the like on the basis of a program predetermined by operating a touch-panel sequence controller 60.

As the radiation therapy unit 1, there can be adopted a radiation therapy unit generally used for radiation therapy. In this embodiment, which is applied to therapy for lung cancers, the beam pathway 1a is fixed at a position aligned to an affected portion 8a, at which carcinomas have grown, of the lung of a patient 8 lying on a bed (treatment table) 7.

The shielding block 2 disposed under the beam pathway 1a may be made from any material insofar as the material can shield the passing of radiation therethrough, and in general, may be preferably configured as a lead block. The size and shape of the shielding block 2 are not particularly limited but can be suitably selected depending on the size and shape of an affected portion. The shielding block 2 in this embodiment is formed into a rectangular parallelopiped shape and has at its center a through-hole as the radiation field 2a. The shielding block and the radiation field formed therein according to the present invention are not limited to those described above but may be configured as follows: namely, a plurality of shielding blocks each having a suitable shape are assembled and are disposed at a position matched to the periphery of an affected portion of a patient lying on a movable plate 32 to be described later in such a manner that a radiation field is formed at a position aligned to the affected portion. When a radiation beam is emitted from the beam pathway 1a, part of the radiation beam passes through the radiation field 2a and reaches the affected portion 8a of the patient 8 lying on the bed (treatment table) 7, and the rest of the radiation beam is shielded by the shielding block 2.

Referring to FIG. 2, the movable portion 3 includes a base plate 30, a pair of rails 31 provided on the upper surface of the base plate 30, the above-described movable plate 32, and a ball screw 34. The base plate 30 has a hole 30a located at a position matched to a movable range of the radiation field 2a of the shielding block 2, that is, the movable range of the affected portion 8a of the patient 8 lying on the bed (treatment table) 7 as shown in FIG. 1, and is mounted to the radiation therapy unit 1 in such a manner as to be located under the beam pathway 1a of the radiation therapy unit 1 as shown in FIG. 1. The movable plate 32 has a hole 32a at a position corresponding to the radiation field 2a and is movably mounted on the rails 31. The shielding block 2 is mounted on the movable plate 32. The ball screw 34 includes a screw shaft 34a rotatably mounted on the base plate 30 via a coupling 33, and a nut 34a screwed with the screw shaft 34a and fixed to a side wall of the movable plate 32. One end side of the screw shaft 34a is connected to a motor shaft (not shown) of the stepping motor 4.

The stepping motor 4 revolves or stops on the basis of a pulse signal fed from the microprocessor. Although a usual motor revolves when a rated voltage is applied thereto, the stepping motor revolves by an angle corresponding to a pulse inputted thereto. In this embodiment, the stepping motor 4 is configured as that having a resolution of 0.36°/pulse; however, the resolution and the like of the stepping motor used in the present invention are not particularly limited.

If the relationship between the pulses and revolution of the stepping motor 4 is set at 1000 pulses/revolution, the stepping motor 4 makes one revolution when 1000 pulses are applied to the driver of the motor. This means 360° (one revolution)/1000 pulses=180°/500 pulses=36°/100 pulses=3.6°/10 pulses=0.36°/1 pulse. The number of revolution of the motor shaft is determined on the basis of the pulse pitch, and the motor shaft is stopped when no pulse is applied thereto. In this way, the stepping motor 4 revolves only by 0.36° when one pulse is applied thereto, and consequently, the revolution of the motor shaft can be controlled with a very fine pitch.

The laser displacement gauge 5, which is fixed over the chest wall of the patient 8, is used for measuring, at a high speed, a distance between the gauge 5 and the chest wall vertically oscillated depending on the respiratory motion. According to the present invention, the kind of the laser displacement gauge is not particularly limited; however, in consideration of the fact that a person generally takes one cycle of inhalation and exhalation for two seconds, the laser displacement gauge may be selected to have a resolution capable of keeping up with a change at the level of a high frequency of 1.5 μm (1 kHz). The synchronized moving radiation shield apparatus A is configured such that a signal detected by the laser displacement gauge 5 is fed to the microprocessor. The fixed position of the laser displacement gauge 5 is not particularly limited but can be set such that the distance between the gauge 5 and the chest wall of the patient is suitable to be measured at a high accuracy, preferably, about 130 mm between the gauge 5 and the center position of the oscillation of the chest wall.

According to the present invention, the measuring portion and the fixed position of the laser displacement gauge are not particularly limited. For example, the vertical oscillation of the belly of a patient may be measured; the oscillation (in the longitudinal direction as viewed from a lying patient) of the shoulder of the patient may be measured by the laser displacement gauge disposed beside the head of the lying patient; or the oscillation of an attachment suitably mounted to the top of the belly of a patient by the laser displacement gauge disposed beside the head of the lying patient.

The laser displacement gauge 5 measures a distance between the gauge 5 and the chest wall of the patient 8 and outputs a distance change in analog voltage. If a distance from the laser displacement gauge 5 and the chest wall of the patient 8 when the patient's exhalation is taken as A and a distance when the patient's inhalation is taken as B, the laser displacement gauge 5 usually outputs a difference between the distances A and B in voltage. For example, for one cycle of respiration of the patient, assuming that the distance A is taken as 153.15 mm (output voltage: 3.26 V) and the distance B is taken as 151.26 mm (output voltage: 3.11 V), a change in distance of 1.89 mm is expressed by a waveform of the voltage as shown in FIG. 3.

The control of the entire radiation therapy unit 1 including the synchronized moving radiation shield apparatus A is performed by the touch-panel sequence controller 60 disposed in an operation room. The controller 60 can be operated and/or monitored by an operational panel 60a. On the other hand, the control of the synchronized moving radiation shield apparatus A about the positional shift of the radiation field matched to the motion of an effected portion, for example, the analog/pulse conversion, pulse division, command to the pulse motor, and the like is performed by the microprocessor contained in the relay control box 61 disposed in a treatment room in which the patient 8 is subjected to radiation therapy.

A physician for subjecting the patient 8 to radiation therapy uses the operational panel 60a of the touch-panel sequence controller 60 for setting conditions of the radiation therapy unit 1, inputting a program data in the microprocessor (to be described later), performing various operations such as starting/ending of operation of the unit, and monitoring the moving state of the synchronized moving radiation shield apparatus A, the position of the affected portion detected by an X-ray simulator, and the like.

The microprocessor converts an analog signal fed from the laser displacement gauge 5 into a pulse signal, and controls the revolution of the stepping motor 4 on the basis of a program which is set such that the pulse number of the pulse signal converted from the analog signal is changed into a pulse number suitable for revolving the stepping motor 4 in such a manner that the affected portion of a patient is aligned to the radiation field, on the basis of a predetermined correlation between the motion of the affected portion and the oscillation of the chest wall of the patient (for example, the movement distance of the affected portion=the oscillation of the chest wall×a).

To be more specific, as a result of measuring the distance between the chest wall of the patient and the laser displacement gauge 5 by the laser displacement gauge 5, the oscillation state of the chest wall is expressed by a waveform of an analog voltage as shown in FIG. 3. For example, the analog signal fed from the laser displacement gauge 5 can be converted into a pulse signal by checking, at 0.005 sec intervals, whether or not the present output voltage from the laser displacement gauge 5 is higher than the previous one by 0.02 V, and outputting one pulse of the pulse signal designating the revolving direction of the motor on the negative side if the present output voltage is higher than the previous one by 0.02 V and outputting one pulse of the pulse signal designating the revolving direction of the motor on the positive side if the present output voltage is lower than the previous one by 0.02 V.

The pulse number of the pulse signal generated by the analog/pulse converter is changed into a pulse number required for revolving the stepping motor on the basis of the above-described program by using a pulse divider if the motion of the affected portion is smaller than the motion of the chest wall or using a pulse multiplier if the motion of the affected portion is larger than the motion of the chest wall.

The coefficient of the pulse divider or pulse multiplier may be desirable to be changed by operating the panel of the touch-panel sequence controller 61. The coefficients of the pulse divider and pulse multiplier are not particularly limited but may be preferably set at about less than 1:100 and about less than 100:1, respectively. If the coefficient of the pulse divider is set at 10:1, 10 pulses converted from the analog signal are changed into one motor pulse, and if the coefficient of the pulse divider is set at 2:1, two pulses converted from the analog signal are changed into one motor pulse. On the other hand, if the coefficient of the pulse multiplier is set at 1:10, one pulse converted from the analog signal is changed into ten motor pulses, and if the coefficient of the pulse multiplier is set at 1:2, one pulse converted from the analog signal is changed into two motor pulses.

The control manner and the configuration of the synchronized moving radiation shield apparatus A are not particularly limited to those described above. For example, a correlation between the oscillation of the chest wall detected by the laser displacement gauge and the motion of the affected portion can be automatically calculated by monitoring, before radiation therapy, the oscillation of the chest wall due to a patient's breathing by the laser displacement gauge and simultaneously monitoring the motion of the affected portion by the X-ray simulator, to determine the distribution of the values measured by the laser displacement gauge and the distribution of the motions of the affected portion measured by the X-ray simulator, and inputting the measured results in the touch-panel sequence controller 60 via the operational panel 60a. As a result, it is possible to automatically set factors necessary for the control program used for analog/pulse conversion and pulse division performed by the microprocessor.

In the synchronized moving radiation shield apparatus A, as shown in FIG. 4, a center photo micro-mark 90 is provided in the hole 32a of the movable plate 32, and a negative side overrun preventive photo micro-mark 91 and a positive side overrun preventive photo micro-mark 91 are provided at positions spaced, by specific distances, from the original position of the movable plate 32 in the longitudinal direction (movement direction). When the front end or rear end is moved up to the overrun preventive photo micro-mark 91, a signal is immediately fed to the microprocessor to automatically stop the radiation therapy unit 1 or generate an alarm. With this configuration, even if the radiation field 2a is intended to overrun in one direction, such overrun of the radiation field 2a can be prevented.

Like in the usual radiation therapy, the synchronized moving radiation shield apparatus A inputs conditions necessary for setting the radiation therapy position of the radiation therapy unit 1, radiation time, and the like in the sequence controller, and when the radiation therapy begins, the synchronized moving radiation shield apparatus A performs the control of the revolution of the stepping motor 4, the control of the moving distance of the movable plate 32, and the like by measuring the oscillation of the chest wall by the laser displacement gauge 5, supplying a detection signal to the microprocessor, analyzing the data by the microprocessor, supplying a command (pulse signal) for controlling the revolution of the motor, and the like.

The synchronized moving radiation shield apparatus A is configured such that the revolution of the stepping motor 4 is mechanically converted into a transverse movement via the ball screw 34. To be more specific, since the screw shaft 34a is fixed to the base plate 30, the nut 34b is moved on the front side or back side of the base plate 30 when the screw shaft 34a is turned. In the case of using the ball screw 34 of a type moved by 20 mm per one turn of the motor shaft, when one pulse is applied to the motor, the motor revolves by 0.36°, with a result that the movable plate is moved by 0.02 mm. Accordingly, on the assumption that the affected portion is moved by 0.02 mm when a differential voltage of 0.02 V is detected by the laser displacement gauge, the movable plate 32 is slid on the rails 31 on the front side or back side of the base plate 30 by 0.02 mm by checking, as described above, the output voltage from the laser displacement gauge 5 at 0.05 sec intervals by the microprocessor, and supplying one pulse of a pulse signal designating the revolving direction of the motor on the negative side if the present voltage is higher than the previous voltage by 0.02 V.

As described above, according to the synchronized moving radiation shield apparatus A, since the microprocessor checks the output voltage from the laser displacement gauge 5 at very short intervals, for example, 0.005 sec intervals to decide the movement direction and stoppage of the radiation field 2a, it is possible to move the radiation field 2a substantially in accordance with the motion of the affected portion 8a during radiation therapy.

By the way, even in the synchronized moving radiation shield apparatus having the above configurations, to cope with occurrence of mismatch between the control of the stepping motor and the motion of an affected portion. To cope with such mismatch, it may be desirable to adopt a configuration that a radiation beam is emitted through the radiation field 2a while the position of the radiation field 2a is checked and also the motion of the affected portion is observed by the X-ray simulator or the like, and if a positional error between the affected portion and the radiation field 2a becomes larger than a specific allowable range, the emission of the radiation beam is manually or automatically interrupted.

In this case, for example, by measuring the distribution of the motions of an affected portion of a patient by the X-ray simulator or the like before radiation therapy and inputting the measured result and the number of respiratory motion in the touch-panel sequence controller 60 via the operational panel 60a, it is possible to automatically calculate a value equivalent to, for example, ±5% of the maximum motion of the affected portion and hence to automatically set the above-described specific allowable range, that is, an allowable range of misalignment between the affected portion and the radiation field.

The present invention is not limited to the above configurations but may be variously changed without departing from the scope of the present invention. For example, the synchronized moving radiation shield apparatus can be configured such that the motion of an effected portion of a patient is previously sampled, and the radiation field is moved by using a servo motor with its revolving speed matched to the sampled data or a cam designed on the basis of the sampled data.

Figure 5:
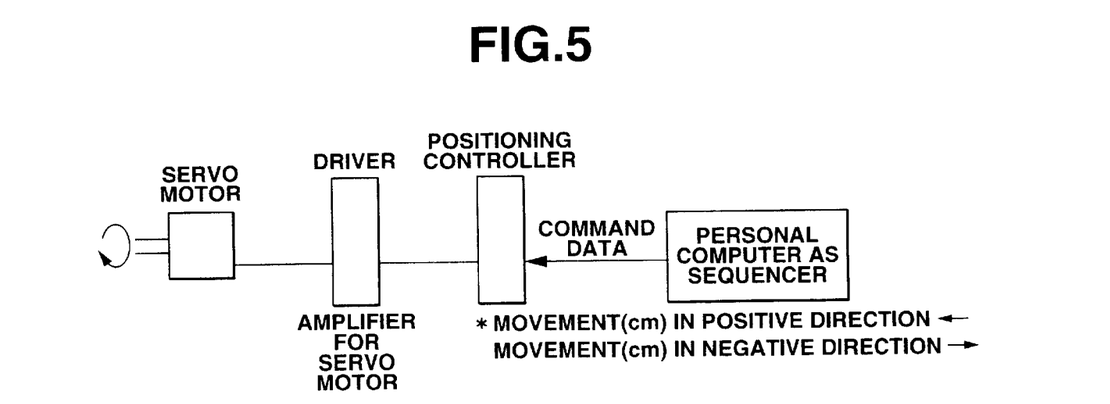
FIG. 5 is a configuration diagram illustrating another embodiment of the synchronized moving radiation shield apparatus of the present invention.

A servo-motor type synchronized moving radiation shield apparatus as another embodiment of the present invention uses a servo motor in place of the stepping motor, and is configured as shown in FIG. 5, in which the revolution of the servo motor is controlled by a personal computer used as a sequencer for instructing the moving direction and the moving distance to a positioning controller, and a driver containing a servo-motor amplifier for revolving the servo motor on the basis of the instruction fed from the positioning controller.

In such a servo motor type apparatus, with a patient's breathing, which includes a state that the patient inhales, a state that the patient exhales, and a state until directly before the patient has the next respiration, taken as one cycle, the revolving speed of the servo motor is programmed for each patient in such a manner as to be matched to the cycle and the movable plate is moved on the program thus determined.

To be more specific, the servo motor type apparatus is operated by inputting the moved amounts based on the sampled data for each patient in the sequencer, feeding the instruction data from the sequencer to the positioning controller, revolving the servo motor by the driver or the servo motor amplifier; and converting the revolution of the servo motor into the transverse motion by the ball screw as described above, to thereby move the movable plate by a distance equivalent to the revolution of the servo motor. It should be noted that such a unit is generally adopted by a robot or machine tool.

Figure 6:
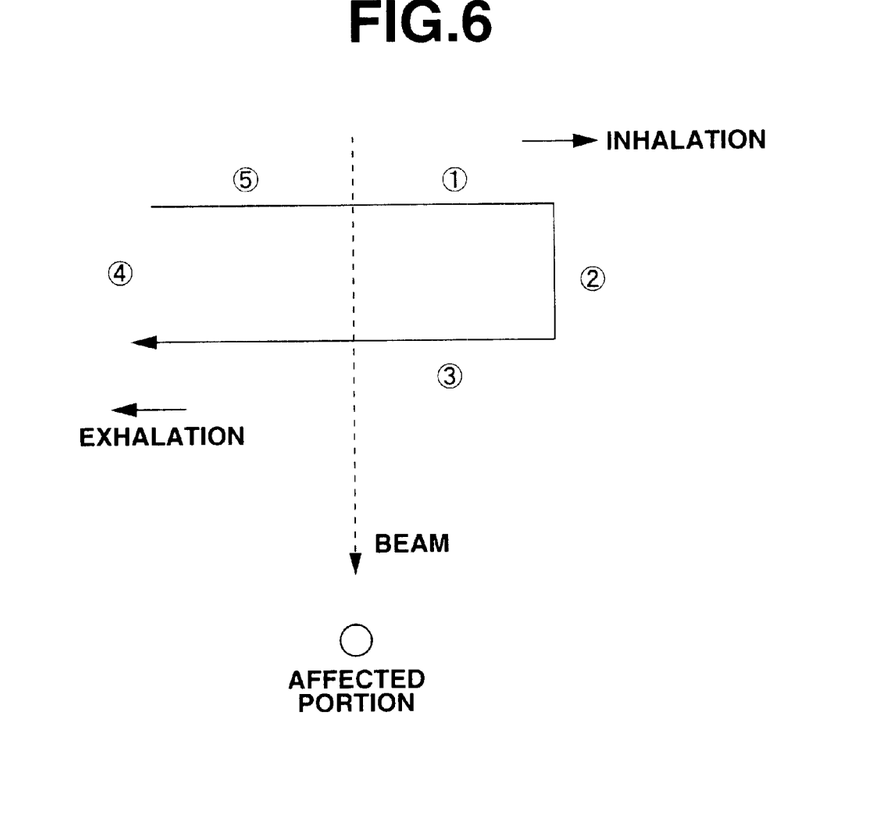
FIG. 6 is a schematic diagram illustrating a program used for the synchronized moving radiation shield apparatus of the present invention.
Figure 7:
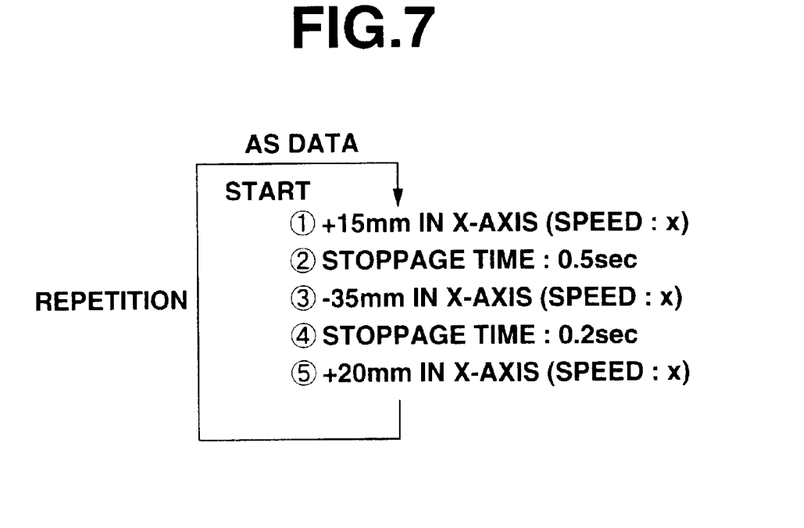
FIG. 7 is a diagram illustrating the content of the program.

In the case of adopting the servo motor type apparatus, as shown in FIG. 6, one cycle of a patient's breathing is divided into a first phase ① that the patient inhales, a second phase ② that the patient stops the inhalation, a third phase ③ that the patient exhales, a fourth phase ④ that the patient stops the exhalation, and a fifth phase ⑤ that the patient starts the inhalation, and sampling data are obtained by radioscopically detecting the position of an affected portion at each of the above phases ① to ⑤. A program shown in FIG. 7 is prepared on the basis of the sampled data thus obtained. Upon radiation therapy of the patient, the radiation field can be moved in such a manner as to be matched to the previously supposed change in position of the affected portion of the patient by inputting the above program in the sequencer, starting the operations of the radiation therapy unit and the synchronized moving radiation shield apparatus, and repeating the program corresponding to the phases ① to ⑤ until a stopping command is fed to the sequencer.

Additionally, in the case of adopting the above method of moving the radiation field on the basis of the previously sampled data, to cope with occurrence of mismatch between the motion of the affected portion and the motion of the radiation field, it may be desirable to adopt a configuration that a radiation beam is emitted through the radiation field 2a while the motion of the affected portion is observed by the X-ray simulator or the like, and if a positional error between the affected portion and the radiation field 2a becomes larger than a specific allowable range, the emission of the radiation beam is manually or automatically interrupted.

Figure 8:
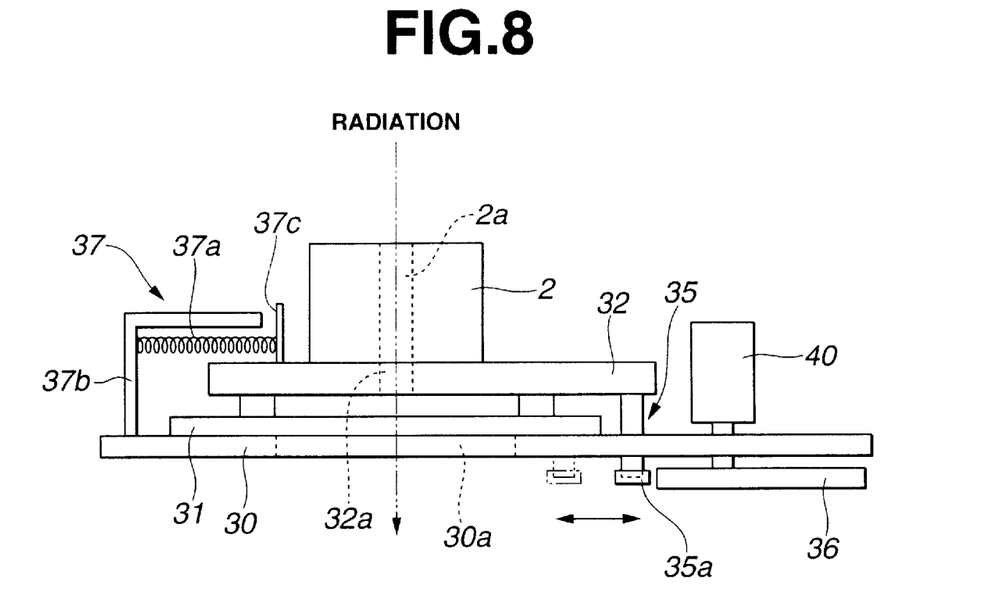
FIG. 8 is a front view illustrating a further embodiment of the synchronized moving radiation shield apparatus of the present invention.

As shown in FIG. 8, the cam type apparatus as a further embodiment of the present invention includes, in place of the combination of the ball screw and stepping motor, a contact portion 35 having a bearing 35a and fixed on the back surface of one end side of the movable plate 32 with the bearing 35a positioned under the base plate 30; a cam 36 disposed with its outer peripheral surface being in contact with the bearing 35a; a motor 40 for rotating the cam 36; and a spring portion 37 fixed to the base plate 30 and the movable plate 32 by fixtures 37b and 37c in such a manner that the movable plate 32 is movable in the biasing direction by the biasing force of a spring 37a.

In such a cam type apparatus, with a patient's breathing, which includes a state that the patient inhales, a state that the patient exhales, and a state until immediately before the the next inhalation, taken as one cycle, the cam 36 is formed in such a manner that the outer peripheral shape of the cam 36 is matched to the cycle for each patient. By using such a cam 36, the movable plate 32 is moved by turning the cam 36 at a constant speed by the motor 40, thereby pressing the bearing 35a by the outer peripheral surface of the cam 36 to push the movable plate 32 in one direction (on the left side in FIG. 8) or returning the movable plate 32 in the opposed direction (on the right side in FIG. 8) by the biasing force of the spring 37a.

Figure 9:
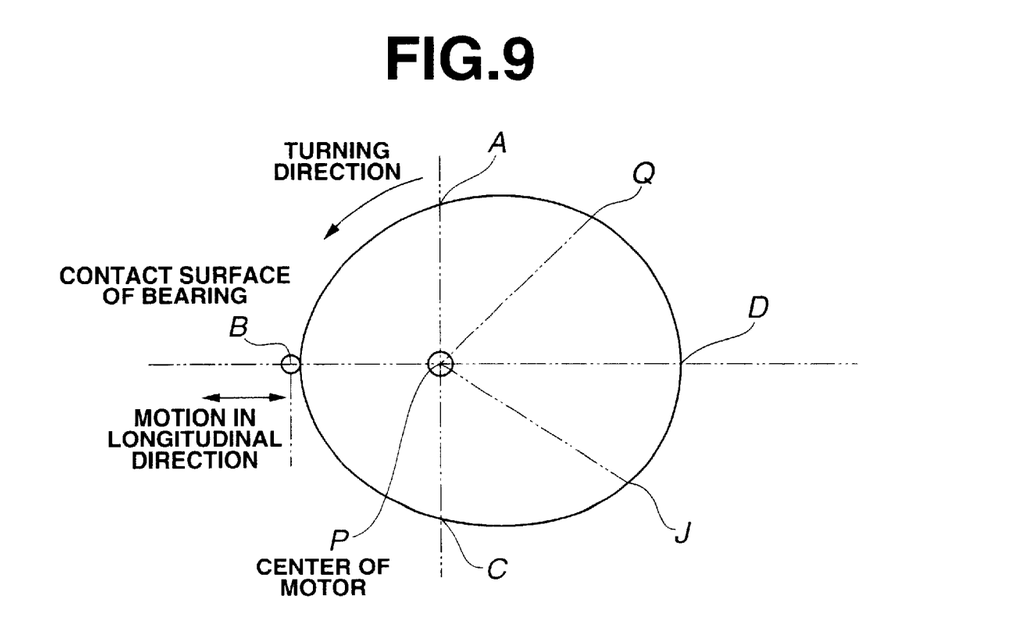
FIG. 9 is a schematic diagram illustrating control means of the synchronized moving radiation shield apparatus.

In the case of designing the cam such that one turn of the cam is equivalent to one cycle of a patient's respiration, if the cam is formed into a true circle, the position of the contact surface between the cam and the bearing is not moved and thereby the radiation field is not moved during one turn of the cam. Accordingly, with a patient's breathing, which includes a state that the patient inhales, a state that the patient exhales, and a state until immediately before the next respiration, taken as one cycle, the motion of an affected portion is sampled at one cycle of respiratory motion, and the shape of the cam is designed on the basis of the sampled data, for example, as shown in FIG. 9. The cam shown in FIG. 9 is designed such that a distance between the motor center P and a position on each of circular-arcs (outer periphery) Q–D and D–J is fixed, and accordingly, the outer peripheral surface of the cam is not moved fore and aft, and the movement of the radiation field can be stopped at a position near a point D.

In the case of adopting the above cam type apparatus, the motor 40 may be configured as a speed control motor capable of allowing the speed change. In this case, if one cycle of a patient's breathing, which includes a state that the patient inhales, a state that the patient exhales, and a state until immediately before the next respiration, takes two seconds, the radiation field can be moved in such a manner as to be matched to the previously sampled motion of the affected portion by setting the number of revolution of the motor at 30 rpm, thereby turning the cam in matching with the respiratory motion to move the movable plate by turn of the cam.

While the above embodiment has been described by way of the example in which the radiation field is moved only in the longitudinal direction or X-direction, the present invention is not limited thereto. As described above, the present invention can be applied to the example in which the radiation field is moved in the longitudinal and lateral directions or XY-directions.

According to the synchronized moving radiation shield apparatus of the present invention, since a radiation field can be moved in such a manner as to be matched to the motion of an affected portion when the affected portion is usually moved even if the patient lies still on a bed upon radiation therapy for carcinoma such as lung cancer or liver cancer, it is possible to prevent adjacent normal portions around the affected portion from being subjected to radiation therapy, and hence to improve the treatment efficiency by increasing the dose of the radiation reaching the affected portion.

While the preferred embodiment of the present invention has been described using the specific terms, such description is for illustrative purposes only, and it is to be understood that changes and variations may be made without departing from the spirit or scope of the following claims.

What is claimed is:

1. A synchronized moving radiation shield apparatus including at least one shielding block disposed under a radiation pathway of a radiation therapy unit in such a manner that a radiation field is formed with said shielding block, wherein an affected portion of a person is exposed to radiation through said radiation field while radiation therapy of a portion, other than said affected portion, of the person, is shielded by said shielding block, said synchronized moving radiation shield apparatus comprising:

a movable portion for movably holding said shielding block while not blocking the passing of radiation through said radiation field;

drive means, connected to said movable portion, for moving said radiation field to a specific position; and control means for controlling said drive means in such a manner that said radiation field is movable in matching to a variation in position of said affected portion, where said control means controls said drive means in such a manner that said radiation field is located at a position corresponding to the affected portion while sequentially estimating the motion of the affected portion.

2. A synchronized moving radiation shield apparatus according to claim 1, further comprising:

detecting means for sequentially detecting a variation in position of part of a body of the person correlated to the motion of the affected portion;

wherein said control means comprises a microprocessor for automatically controlling said drive means on the basis of a detection value of said detecting means in accordance with a program for realizing alignment of the affected portion to said radiation field.

3. A synchronized moving radiation shield apparatus according to claim 1, wherein said movable portion comprises:

a base plate having a hole at a position matched to a movable range of said radiation field and fixed under said radiation therapy unit;

rails provided on the upper surface of said base plate; and a movable plate having a hole at a position corresponding to said radiation field and movably disposed on said rails;

wherein said shielding block is mounted on said movable plate in such a manner that said radiation field is formed in said shielding block, and said movable plate is moved by said drive means.

4. A synchronized moving radiation shield apparatus according to any one of claim 1, wherein said drive means comprises a stepping motor revolving on the basis of a pulse signal fed from said control means.

5. A synchronized moving radiation shield apparatus according to any one of claim 1, further comprising detecting means for detecting the fact that said movable portion is moved up to a critical position of said movable range.

* * * * *